US012723256B2

(12) United States Patent
Mande et al.

(10) Patent No.: US 12,723,256 B2
(45) Date of Patent: Sep. 1, 2026

(54) SYSTEM AND METHOD FOR COMBATING PLANT PATHOGENIC BACTERIAL INFECTIONS

(71) Applicant: Tata Consultancy Services Limited, Mumbai (IN)

(72) Inventors: Sharmila Shekhar Mande, Pune (IN); Swadha Anand, Pune (IN); Preethi Alagarai Sampath, Pune (IN)

(73) Assignee: Tata Consultancy Services Limited, Mumbai (IN)

( * ) Notice: Subject to any disclaimer, the term of this patent is extended or adjusted under 35 U.S.C. 154(b) by 1304 days.

(21) Appl. No.: 17/596,194

(22) PCT Filed: Jun. 5, 2020

(86) PCT No.: PCT/IB2020/055321
§ 371 (c)(1),
(2) Date: Dec. 3, 2021

(87) PCT Pub. No.: WO2020/245793
PCT Pub. Date: Dec. 10, 2020

(65) Prior Publication Data

US 2022/0380795 A1 Dec. 1, 2022

(30) Foreign Application Priority Data

Jun. 6, 2019 (IN) ............................ 201921022526

(51) Int. Cl.

*G16B 30/10* (2019.01)
*C12N 15/82* (2006.01)
*C12Q 1/689* (2018.01)
*G16B 20/00* (2019.01)
*G16B 50/10* (2019.01)

(52) U.S. Cl.
CPC ......... *C12N 15/8281* (2013.01); *C12Q 1/689* (2013.01); *G16B 20/00* (2019.02); *G16B 30/10* (2019.02); *G16B 50/10* (2019.02); *C12Q 2600/158* (2013.01)

(58) Field of Classification Search
None
See application file for complete search history.

(56) References Cited

U.S. PATENT DOCUMENTS

| | | | |
|---|---|---|---|
| 8,329,988 | B2 | 12/2012 | Frank et al. |
| 9,357,785 | B2 | 6/2016 | Gonzalez et al. |
| 10,930,367 | B2 | 2/2021 | Zhang et al. |
| 2015/0356239 | A1 | 12/2015 | Zhang et al. |
| 2018/0181702 | A1 | 6/2018 | Mande et al. |

FOREIGN PATENT DOCUMENTS

| | | | |
|---|---|---|---|
| EP | 1002134 | B1 | 9/2006 |
| WO | WO2014164694 | A1 | 10/2014 |
| WO | WO2018/064208 | A1 | 4/2018 |

OTHER PUBLICATIONS

Capote, Nieves et al., "Molecular Tools for Detection of Plant Pathogenic Fungi and Fungicide Resistance", Title of the item: Plant Pathology, Date: Apr. 2012, Publisher: Intech Open, https://www.intechopen.com/chapters/34844.
GenBank Accession No. CP001964.1 Cellulomonas flavigena DSM 20109, complete genome. Jan. 28, 2014 [online]. [Retrieved on Jun. 23, 2021]. Retrieved from the internet: <URL: https://www.ncbi.nlm.nih.gov/nuccore/CP001964.1 >. Entire document.
GenBank Accession No. HM212510.1 Asaccus elisae voucher CAS218143 recombination activating protein 1 (RAG1) gene, partial eds. Jul. 25, 2016 [online] [Retrieved on Jun. 23, 2021]. Retrieved from the internet: <URL: https://www.ncbi.nlm.nih.gov/nuccore/HM212510>, whole document.
International Search Report and Written Opinion mailed Jul. 22, 2021, in International Application No. PCT/IB2020/055321; 6 pages.

*Primary Examiner* — Joseph Woitach
(74) *Attorney, Agent, or Firm* — Finnegan, Henderson, Farabow, Garrett & Dunner, LLP

(57) ABSTRACT

Bacterial plant pathogens such as *Xanthomonas* sp. and *Pseudomonas syringae* are developing resistance to various classes of antibiotics. A method and system for combating plant pathogenic bacterial infections have been provided. The system is configured to provide strategies to combat infections in plants caused by multi-drug resistant (MDR) plant pathogens. The strategy involves identifying potential target sites in the plant pathogen, which can be utilized to compromise its multiple virulence or essential functions at the same time. The idea used in this disclosure utilizes the fact that a conserved stretch of nucleotide sequence occurring multiple times on a pathogen genome in genomic neighborhood of genes encoding virulence factors or in vicinity of genes essential for pathogen survival encoded within the genome of the candidate pathogen can be targeted to disrupt the overall genetic machinery of the plant pathogen.

17 Claims, 7 Drawing Sheets

Specification includes a Sequence Listing.

*Pseudomonas syringae / Xanthomonas axonopodis* genome

- RPSEUDO-S / RXAN

- Virulent / essential genes

FIG. 2

Enzymatic cleavage in either directions

```
SEQUENCE LISTING

<160> NUMBER OF SEQ ID NOS: 2

<210> SEQ ID NO 1
<211> LENGTH: 52
<212> TYPE: DNA
<213> ORGANISM: Pseudomonas syringae
<220> FEATURE:
<221> NAME/KEY: misc_feature
<222> LOCATION: (29)..(29)
<223> OTHER INFORMATION: n is a, c, g, or t

<400> SEQUENCE: 1

ggacgcgaga gcgtccagga acggcatgnc gacgcaggag cgtcgcacga ta           52


<210> SEQ ID NO 2
<211> LENGTH: 22
<212> TYPE: DNA
<213> ORGANISM: Xanthomonas axonopodis
<220> FEATURE:
<221> NAME/KEY: misc_feature
<222> LOCATION: (20)..(20)
<223> OTHER INFORMATION: n is a, c, g, or t

<400> SEQUENCE: 2

ggacggcagt ccatgctcgn ca                                            22
```

SYSTEM AND METHOD FOR COMBATING PLANT PATHOGENIC BACTERIAL INFECTIONS

PRIORITY CLAIM

The present application is a U.S. National Stage Filing under 35 U.S.C. § 371 and claims priority from International Application No. PCT/IB2020/055321 filed on Jun. 5, 2020, which application claims priority under 35 U.S.C. § 119 from Indian provisional application No. 20/192,1022526, filed on Jun. 6, 2019. The entire contents of the aforementioned applications are incorporated herein by reference.

REFERENCE TO SEQUENCE LISTING SUBMITTED ELECTRONICALLY

An official copy of the sequence listing is submitted electronically via EFS-WEB as an ASCII formatted sequence listing with a file named 17596194-sequence-listing.txt, having a size of 1 KB. The sequence listing contained in this ASCII formatted document is part of the specification and is herein incorporated by reference in its entirety.

TECHNICAL FIELD

The embodiments herein generally relates to the field of plant pathogenic bacterial infections, and, more particularly, to a method and system for combating the problem of multidrug resistance resulting due to infection by plant pathogens.

BACKGROUND

In the recent years, there has been a need for higher crop yield across the globe to keep up with the demands of the increasing population. However, the annual crop production is severely reduced because of various environmental causes such as weeds, pests and diseases. Of these, diseases caused by bacterial infection plays a prominent role. Antibiotics (mostly streptomycin and oxytetracycline) are used primarily as prophylactic (a preventive measure before the actual occurrence of the disease) treatments to combat infections caused by plant pathogenic bacteria. The rampant use of these antibiotics have led to major antimicrobial resistance (AMR) in the plant pathogens. Studies have shown that streptomycin resistance is widespread among the plant pathogens.

Two such bacterial plant pathogens that are developing resistance to various classes of antibiotics at an alarming rate are *Xanthomonas* sp. (which causes citrus cranker disease in crops) and *Pseudomonas syringae* (which causes blight disease in crops). A study conducted in 2014 has shown that *Xanthomonas axonopodis* is fully resistant to cefotaxime and shows moderate resistance to gentamicin. It should be noted that gentamicin is of importance due to its predominant use against human pathogens. A possibility exists for transfer of gentamicin resistance to human pathogens. *Pseudomonas syringae* has also shown increased resistance to various antibiotics used in human therapeutics such as ampicillin, rifampicin, chloramphenicol to name a few.

These antibiotic resistance genes in the plant pathogens are further transferred between different bacteria utilizing several transfer methods. Additional problems arise which pertain to formation of biofilms in these bacteria which allows them to evade antibiotics. Several studies have shown that biofilm formation inhibitors (like several enzymes which degrade the matrix) as well as quorum quenchers (prevent biofilm formation) can prove useful in this regard. Despite utilizing these inhibitors several bacteria still escape the antibiotics and lead to relapse once the treatment is stopped.

In addition to that, immunological and antisense approach has also been used. These treatments often lose their efficacy as bacteria often mutate the pathogenic factors used as targets thereby escaping the immune machinery of the host.

SUMMARY

Embodiments of the present disclosure present technological improvements as solutions to one or more of the above-mentioned technical problems recognized by the inventors in conventional systems. For example, in one embodiment, a system for combating infections due to plant pathogen has been provided. The system comprises a sample collection module, a pathogen detection and DNA extraction module, a sequencer, one or more hardware processors, a memory, an administration module and an efficacy module. The sample collection module obtains a sample from an infected area. The pathogen detection and DNA extraction module isolates DNA from the obtained sample using one of a laboratory methods. The sequencer sequences the isolated DNA. The memory in communication with the one or more hardware processors, wherein the one or more first hardware processors are configured to execute programmed instructions stored in the one or more first memories, to: identify a set of nucleotide repeat sequences in the sequenced DNA which occur more than a predefined number of times in the plant pathogen; identify a set of neighborhood genes present upstream and downstream of the set of nucleotide repeat sequences; annotate the set of neighborhood genes according to their functional roles in their respective pathogen based on their involvement in pathways in the identified set of neighborhood genes; and test the presence of a secondary structure in the identified set of nucleotide repeat sequences. The administration module prepares and administers an engineered polynucleotide construct on the infected plant to combat the infections due to the plant pathogen, wherein the engineered polynucleotide construct is comprising: one or more of a set of nucleotide repeat sequences with multiple copies dispersed in nucleotide sequences of genomes of *Pseudomonas syringae* or *Xanthomonas axonopodis*, wherein the set of nucleotide repeat sequences comprises one or more of a Sequence ID 001, reverse complement of the Sequence ID 001, Sequence ID 002, reverse complement of the Sequence ID 002, a first enzyme capable of nicking and cleaving the identified set of nucleotide repeat sequences, and a second enzyme capable of removal of a set of neighborhood genes flanking the set of nucleotide repeat sequences. The efficacy module checks the efficacy of the administered engineered polynucleotide construct to combat the plant pathogen after a predefined time period; and re-administer the engineered polynucleotide construct if the plant pathogen is still present in the infected plant post administering.

In another aspect, a method for combating infections due to plant pathogen, the method comprising. Initially, a sample is obtained from an infected plant. Later, DNA is isolated and extracted from the obtained sample using one of a laboratory methods. Further, the isolated DNA is sequenced to get a characterized sample. In the next step, a set of nucleotide repeat sequences is identified in the sequenced DNA which occur more than a predefined number of times in the plant pathogen. Further, a set of neighborhood genes is identified present upstream and downstream of the set of nucleotide repeat sequences. In the next step, the set of neighborhood genes is annotated according to their functional roles in their respective pathogen based on their involvement in pathways in the identified set of neighborhood genes. Further, the presence of a secondary structure is tested in the identified set of nucleotide repeat sequences. Later, an engineered polynucleotide construct is prepared and administered on the infected plant to combat the infections due to the plant pathogen, wherein the engineered polynucleotide construct is comprising: one or more of a set of nucleotide repeat sequences with multiple copies dispersed in nucleotide sequences of genomes of *Pseudomonas syringae* or *Xanthomonas axonopodis*, wherein the set of nucleotide repeat sequences comprises one or more of a Sequence ID 001, reverse complement of the Sequence ID 001, Sequence ID 002, reverse complement of the Sequence ID 002, a first enzyme capable of nicking and cleaving the identified set of nucleotide repeat sequences, and a second enzyme capable of removal of a set of neighborhood genes flanking the set of nucleotide repeat sequences. In the next step, the efficacy of the administered engineered polynucleotide construct is checked to combat the plant pathogen after a predefined time period. And finally, the engineered polynucleotide construct is re-administered if the plant pathogen is still present in the infected plant post administering.

In an aspect, the target sites or nucleotide repeat sequences in this disclosure refer to nucleotide sequences which repeat a minimum number of ten times within the genome of the candidate pathogen/pathogens which are identified in an infected site from which the sample is collected. These nucleotide repeat sequences can be targeted in order to debilitate the pathogen. The mentioned nucleotide repeat sequence/sequences is selected if it occurs more than 10 times in all the pathogenic strains of the candidate specie or genus to which the candidate pathogen/pathogens identified in an infected site belong. The nucleotide repeat sequence is selected such that it does not occur more than twice in genomes of strains belonging to any other genus than that of the candidate pathogen and does not occur more than twice within the genome of the host.

In yet another aspect, one or more non-transitory machine readable information storage mediums comprising one or more instructions which when executed by one or more hardware processors cause combating infections due to plant pathogen, the method comprising. Initially, a sample is obtained from an infected plant. Later, DNA is isolated and extracted from the obtained sample using one of a laboratory methods. Further, the isolated DNA is sequenced to get a characterized sample. In the next step, a set of nucleotide repeat sequences is identified in the sequenced DNA which occur more than a predefined number of times in the plant pathogen. Further, a set of neighborhood genes is identified present upstream and downstream of the set of nucleotide repeat sequences. In the next step, the set of neighborhood genes is annotated according to their functional roles in their respective pathogen based on their involvement in pathways in the identified set of neighborhood genes. Further, the presence of a secondary structure is tested in the identified set of nucleotide repeat sequences. Later, an engineered polynucleotide construct is prepared and administered on the infected plant to combat the infections due to the plant pathogen, wherein the engineered polynucleotide construct is comprising: one or more of a set of nucleotide repeat sequences with multiple copies dispersed in nucleotide sequences of genomes of *Pseudomonas syringae* or *Xanthomonas axonopodis*, wherein the set of nucleotide repeat sequences comprises one or more of a Sequence ID 001, reverse complement of the Sequence ID 001, Sequence ID 002, reverse complement of the Sequence ID 002, a first enzyme capable of nicking and cleaving the identified set of nucleotide repeat sequences, and a second enzyme capable of removal of a set of neighborhood genes flanking the set of nucleotide repeat sequences. In the next step, the efficacy of the administered engineered polynucleotide construct is checked to combat the plant pathogen after a predefined time period. And finally, the engineered polynucleotide construct is re-administered if the plant pathogen is still present in the infected plant post administering.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles:

Figure 2:
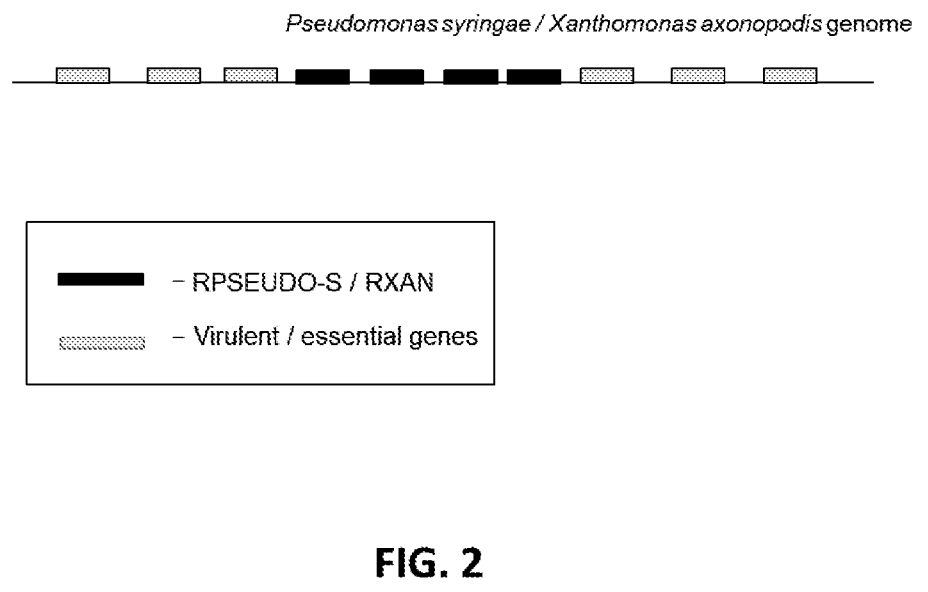

FIG. 2 shows nucleotide repeat sequences along with neighborhood genes in the *Pseudomonas syringae* and *Xanthomonas axonopodis* genomes according to an embodiment of the disclosure.

DETAILED DESCRIPTION

Figure 1:
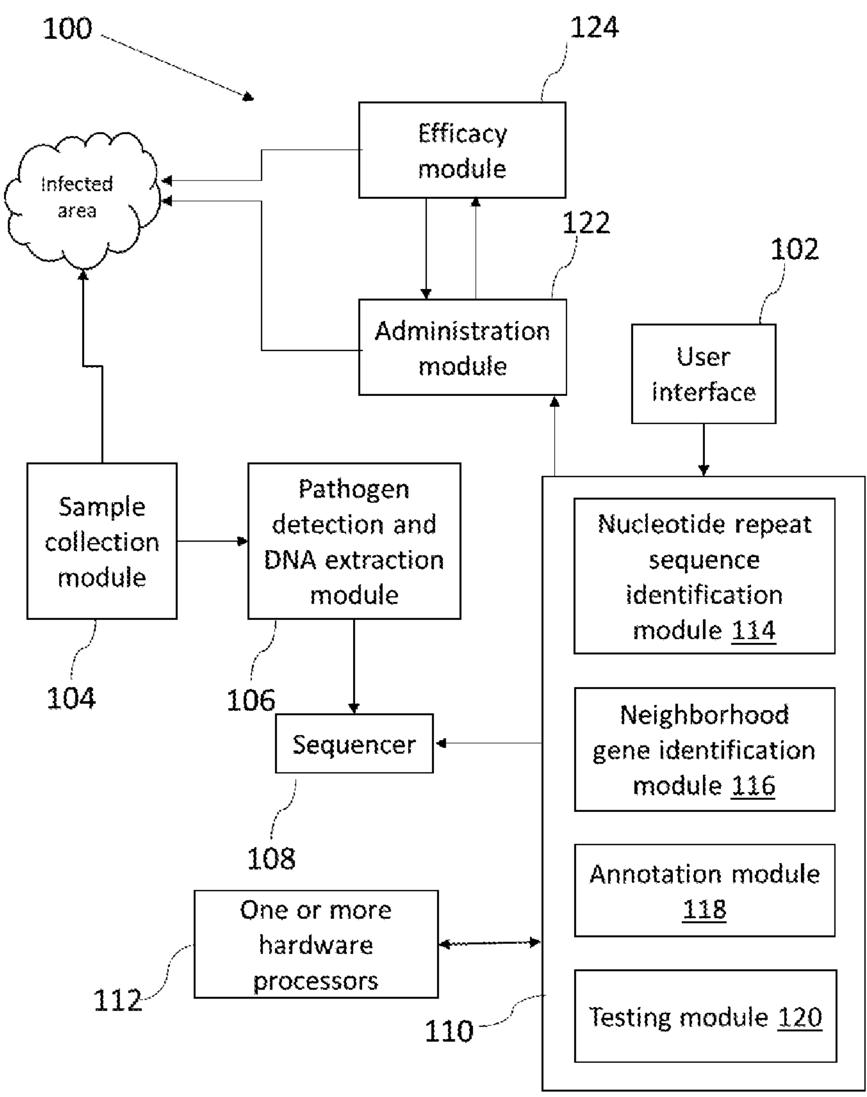
FIG. 1 illustrates a block diagram of a system for combating infections due to a plant pathogen according to an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Glossary—Terms Used in the Embodiments

The expression "nucleotide repeat sequences" or "repeated nucleotide sequences" or "the set of nucleotide repeats" or "repeat element" or "repeated sequence regions" or "target sequence" or "target sites" or "similar sequence stretches" in the context of the present disclosure refers to nucleotide sequences which have been repeated multiple times in a sequence of DNA extracted from a sample obtained from the infected plant or within nucleotide sequence obtained for a genome of a pathogen.

The term "metagenome" refers to the genetic material derived directly from the infected site and can be considered representative of overall microorganisms present in a sample collected from an environment. The information about metagenome and its taxonomic constitution is obtained by either sequencing the genes considered as markers for different taxa (For example 16S rRNA), amplifying genes of interest using specific primers through methods like but not limited to Polymerase Chain Reaction (PCR). This information can also be obtained by whole genome sequencing of the obtained environmental or metagenomic sample. The sample collected from the environment is referred to from now on as metagenomic sample.

The term "identified nucleotide repeat sequence is dispersed across distant locations in the pathogen genome" refers to the fact that the nucleotide sequences identified in this method are spread at distant locations across the pathogen genome and is not clustered together at one particular location alone on the genome.

In this disclosure, the terms "distant location" or "distinct location" or "dispersed sequences" refer to locations of two nucleotide repeat sequences that are separated by >10000 base pairs. Nucleotide repeat regions having distance less than 10000 base pairs between their locations have been considered as clustered repeats.

The expression "candidate genus" or 'candidate pathogen' refers to the genus, specie or pathogen in which the nucleotide repeat sequence is identified and is used as a target sequence/site.

The term "commensal" refers to microbes which are considered beneficial to the host or cause no harm to the host.

The term 'pathogen' refers to microbe/microbes which cause a disease in host.

The term 'host' refers to either a living organism or an environmental site. In an embodiment, 'host' may refer to human, animal or plant in which a pathogenic infection may be observed.

The term 'non-culturable' refers to microbes that cannot be grown in a laboratory settings because the ideal conditions and media for their growth is not well characterized. Such microbes can be analyzed by culture independent methods discussed in various embodiments of the disclosure.

Majority of the existing methods for combating pathogens focus on silencing specific genes in order to curtail their expression. Targeting single functional aspects of bacteria often is not sufficient as bacteria might mutate the targets and develop resistance to the therapeutic intervention. To overcome the drawbacks of the existing methods, the present system and method deals with identifying and targeting multiple copies of a nucleotide repeat sequence at distant locations on the genome as well as the important functional genes flanking this sequence. Therefore, the method allows to debilitate multiple important functions of the pathogen simultaneously. The important functional genes in this disclosure refer to the genes in pathogens which encode for proteins which are critical for survival, pathogenicity, interaction with the host, adherence to the host or for the virulence of bacteria. Development of resistance in pathogens to the method mentioned in this disclosure is difficult as the pathogen will have to bring about multiple mutations in distant locations. The present disclosure includes targeting multiple virulence and essential proteins of pathogens. The method may also include targeting various other proteins performing important functions (metabolism, host interactions, pathogenicity etc.) in bacteria.

Referring now to the drawings, and more particularly to FIG. 1 through FIG. 6B, where similar reference characters denote corresponding features consistently throughout the figures, there are shown preferred embodiments and these embodiments are described in the context of the following exemplary system and/or method.

According to an embodiment of the disclosure, a system 100 for combating infections in plants due to plant pathogens is shown in the block diagram of FIG. 1. The system 100 is configured to provide strategies to combat infections in plants caused by multi-drug resistant (MDR) plant pathogens. The strategy involves identifying potential target sites in the plant pathogen, which can be utilized to compromise its multiple virulence or essential functions at the same time. The idea used in this disclosure utilizes the fact that a conserved stretch of nucleotide sequence occurring multiple times on a pathogen genome in genomic neighbourhood of genes encoding virulence factors or in vicinity of genes essential for pathogen survival encoded within the genome of the candidate pathogen can be targeted to disrupt the overall genetic machinery of the plant pathogen. These nucleotide repeat sequences might also lie in the neighborhood of genes which perform other critical functions in a pathogen.

In the present disclosure genomic neighbourhood or vicinity or 'flanking genes' refers to regions lying within a predefined number of genes to the selected nucleotide repeat sequence (or its reverse complement) on the nucleotide sequence of the candidate pathogen genome or within a distance of predefined number of bases with respect to the selected nucleotide repeat sequence (or its reverse complement) on the nucleotide sequence of the pathogen genome. The flanking genes are found on each strand on pathogen genomic DNA. In an embodiment the genomic neighbourhood or flanking genes may comprise of 10 genes lying on either side of nucleotide repeat sequence or its reverse complement in terms of its location on the pathogen genome. The reverse complement of target sequence is obtained by interchanging letters A and T and interchanging letters C and G between target and complement sequence. The reverse complement refers to the sequence corresponding to the identified nucleotide repeat sequence in the opposite strand of DNA.

A conserved stretch of sequence refers to a nucleotide repeat sequence which occurs within all pathogenic genomes belonging to a candidate genus. Another important factor would be occurrence of these sequences only in the genomic sequence of multiple pathogenic strains of candidate plant pathogen and minimum cross reactivity with the commensals (belonging to same candidate genus or other genera) as well as the host. Cross reactivity, in this disclosure, refers to the occurrence of these conserved stretches of nucleotide sequences more than twice in the host genome or more than twice in genera other than the candidate genus or more than twice within commensal bacteria belonging to the candidate genus for which this sequence is being utilized as a target. Further, the identified potential target sites in the plant pathogen are not specific to a single strain of the pathogen. In most cases, metagenomic samples contain bacteria whose strain level information cannot be obtained. Thus, the method can be utilized to target all strains of plant pathogens in the given candidate genus/species of the bacteria and is not hindered by the absence of strain level information.

The present disclosure have been specifically explained on the sequenced genomes of *Pseudomonas syringae* and *Xanthomonas axonopodis*. *Xanthomonas axonopodis* causes citrus cranker disease in crops and *Pseudomonas syringae* causes blight disease in crops. *Pseudomonas syringae* has also shown increased resistance to various antibiotics used in human therapeutics such as ampicillin, rifampicin, chloramphenicol etc.

According to an embodiment of the disclosure, the system 100 consists of a user interface 102, a sample collection module 104, a pathogen detection and DNA extraction module 106, a sequencer 108, a memory 110 and a processor 112 as shown in FIG. 1. The processor 112 is in communication with the memory 110. The memory 110 further includes a plurality of modules for performing various functions. The memory 110 may include a nucleotide repeat sequence identification module 114, a neighborhood gene identification module 116, an annotation module 118 and a testing module 120. The system 100 further comprises an administration module 122 and an efficacy module 124 as shown in the block diagram of FIG. 1.

According to an embodiment of the disclosure, the sample is collected from the infected plant using the sample collection module 104. In this module, the method utilized for extracting samples from the infected sites depends largely on the site of infection. In an embodiment where the site of infection is in plants (for example, citrus cranker caused by *Xanthomonas axonopodis*), samples can be obtained from the whole plant or plant parts such as root, stem, leaf, seeds, fruits etc. Using a whole plant for sample collection may be better suited to identify the pathogen unless it is clearly known that the disease affects only a particular part. Soil samples within the top 10 cm of the root zone in and around the infected root of the plant can also be collected to identify the disease pathogen. Any other laboratory accepted method of sample extraction/collection from environment as well as the plant is within the scope of this invention.

DNA is isolated and then extracted from the sample using laboratory standardized protocol using the pathogen detection and DNA extraction module 106 and sequencing is performed using the sequencer 108. It should be appreciated, that the bacterial cells are isolated from the extracted sample before being presented to the pathogen detection and DNA extraction module 106 in cases where the pathogen is known to be culturable. In case of non-culturable pathogen, the collected samples are directly processed to the pathogen detection and DNA extraction module 106, DNA/RNA is isolated and extracted from the sample using laboratory standardized protocols using the pathogen detection and DNA extraction module 106 and sequencing is performed using the sequencer 108. The nucleotide sequences obtained after sequencing of extracted DNA/RNA sequences are then provided to the processor 112 using the user interface 102. The nucleotide sequences can be obtained for 16S rRNA, a nucleotide sequence encoding for any particular protein of interest being amplified, or sequences corresponding to DNA fragments for whole genome sequencing or shotgun sequencing. In one embodiment, DNA/RNA can be extracted using miniprep isolation kits and other methods standardized in laboratory setups. The extracted DNA is then provided into the sequencer 108 and the sequences so obtained are fed into the processor 112 using the user interface 102. The user interface 102 is operated by a user. The user interface 102 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite.

The pathogen detection and DNA extraction module 106 is also configured to utilize experimental techniques to detect pathogens present in an infected site. The use of any laboratory acceptable methods of detecting presence of pathogens present at the infected site is within scope of the disclosure. In one embodiment, presence of viable living cells can be detected by utilizing presence of bacterial mRNA which has a short half-life and will not exist once the cells are dead. This mRNA based method may involve identifying antigen/protein specific for the pathogen which can be utilized as a marker for that pathogen and produced by the pathogen in abundance and the corresponding gene on the pathogen genome can be obtained. The mRNA corresponding to expression of these genes can be detected using techniques like but not limited to polymerase chain reaction (RT-PCR) assays or reverse transcriptase strand displacement amplification (RT-SDA) assays. In another embodiment, expression of proteins identified as specific to these pathogens can be detected using various laboratory accepted methods for protein purification and detection. Chromogenic enzyme assays for a pathogen are also within scope of the invention. Specific metabolites or compounds produced by a pathogen can also be detected (using different laboratory acceptable methods like Mass spectrometry, HPLC-MS, spectrometry-based methods etc.) to ascertain pathogen presence. In other embodiments, the identified antigens/marker sequences (e.g. sequence-characterized amplified region (SCAR) markers in *Xanthomonas axonopodis*) can be targeted using methods like nucleic acid amplification tests (NAAT), real time PCR, immunoassays (For example xcd108 antibody for *Xanthomonas axonopodis*) etc. as well as specific staining and microscopy techniques and flow cytometry methods of detecting pathogens are also within scope of this invention. PCR or Restriction Fragment Length Polymorphism (RFLP) based detection of 16S rRNA in order to identify pathogens can also be utilized. In one more embodiment, staining methods can also be utilized to identify a pathogen and establish viability of a pathogen cell (e.g. propidium iodide can be used for identifying dead cells). Cell toxicity assays can also be utilized for toxins based detection of pathogens. Further in case of sporulating bacteria, spore detection assays can also be utilized. In case of culturable bacteria, the viability of pathogens can even be established using culturing methods using selective media followed by methods to detect specific pathogens discussed above. In another embodiment, the presence of pathogens can be estimated using phenotypic traits or symptoms of a disease. For example citrus canker often associated with presence of *P. syringae* can be determined by whitish or reddish exudates oozing on the trunks and branches, spots on leaves, browning of buds and flowers and misshapen fruits. Any other method of detecting pathogens are also within scope of this disclosure.

According to an embodiment of the disclosure, the pathogen detection and DNA extraction module 106 is configured to applying one or more techniques for identification or detection of microbes in a collected sample comprising a sequencing technique, a flow cytometry based methodology, a microscopic examination of the microbes in collected sample, microbial culture of pathogens in vitro, immunoassays, cell toxicity assay, enzymatic, colorimetric or fluorescence assays, assays involving spectroscopic/spectrometric/chromatographic identification and screening of signals from complex microbial populations, The pathogen or microbial characterization data may comprise one or more of sequenced microbial DNA data, a Microscopic imaging data, a Flow cytometry cellular measurement data, a colony count and cellular phenotypic data of microbes grown in in-vitro cultures, immunological data, proteomic/metabolomics data, and a signal intensity data. The sequenced microbial data from sequencer may comprises one or more of sequences obtained from next generation sequencing platforms comprising marker genes including 16S rRNA, Whole Genome Shotgun (WGS) sequencing, a fragment library based sequencing technique, a mate-pair library or a paired-end library based sequencing technique, or a combination thereof. The sequencing data may also comprise of complete genome sequences of the pathogens obtained within a collected sample. In one embodiment, the taxonomic groups or pathogens within a sample collected can be obtained by amplification of marker genes like 16S rRNA within bacteria. In another embodiment, the taxonomic groups or pathogens within a sample can be obtained by the binning of whole genome sequencing reads into various taxonomic groups using different methods including sequence similarities as well as several methods using supervised and unsupervised classifiers for taxonomic binning of metagenomics sequences.

According to an embodiment of the disclosure, the processor 112 comprises the nucleotide repeat sequence identification module 114. The nucleotide repeat sequence identification module 114 is configured to identify a set of nucleotide repeat sequences in the extracted DNA which occur more than a predefined number of times (refers to the number of occurrences of nucleotide repeat sequence on a genome in a dispersed manner and this number might vary with system and pathogen under consideration) in the genome and are dispersed at distant locations on the genome. The predefined number refers to the number of occurrences of nucleotide repeat sequence on the genomic sequences of all pathogenic strains of candidate pathogen in a dispersed manner and this number might vary with system and pathogen under consideration. A minimum of 10 occurrences is required for a nucleotide repeat sequence to be considered. In an example, RPSEUDO-S is identified for *Pseudomonas syringae* and RXAN is identified for *Xanthomonas axonopodis*. RPSEUDO-S/RXAN is shown in schematic representation of FIG. 2. Further, it is important to ensure that the identified respective nucleotide sequence region is specific to a particular candidate pathogenic genus only and, on nucleotide based sequence alignment, shows no more than two cross matches with commensals of the other genera or commensals within same genus. Cross match refers to the occurrence of identified nucleotide repeat sequence region more than two times in a genus which is different from the candidate genus in which the nucleotide repeat sequence has been identified as is to be used as a target site.

In addition to that, the identified set of nucleotide repeat sequences are not specific to a single strain of the pathogen. For example, RPSEUDO-S is present in multiple pathogenic strains of *Pseudomonas syringae* and RXAN is present in multiple pathogenic strains of *Xanthomonas axonopodis*. In most cases, metagenomic samples contain bacteria whose strain level information cannot be obtained. Thus, the method can be utilized to target all pathogens in the given species of the bacteria and is not hindered by the absence of strain level information and making it more robust.

Following method can be used for the identification of the repeat sequence region.

Conserved nucleotide repeat elements were identified on *Pseudomonas syringae* and *Xanthomonas axonopodis* genomes by taking sequence stretches of predefined length Rn (50-70 for *Pseudomonas syringae* and 30-50 for *Xanthomonas axonopodis* in this embodiment) picked from the genome sequence of candidate pathogen or different strains of candidate pathogen, keeping the difference in the start position of two consecutive nucleotide sequence stretches $R_{ni+1}$ and $R_{ni}$ as 5 nucleotides. Predefined length Rn refers to the length of a stretch of nucleotide sequence (picked from the complete nucleotide sequence of a bacterial genome) used as a seed input for local sequence alignment tools. This predefined length may differ depending on the pathogen. In the next step, a reference genome based nucleotide sequence alignment tool is applied in order to align the sequence stretch with nucleotide sequences corresponding to genomes of all pathogenic strains belonging to the candidate pathogen, genus or specie. In this implementation, stretches of both the identified nucleotide repeat sequences RPSEUDO-S and RXAN were aligned within the genome by local alignment as implemented in PILER software to find the location of these elements in all sequenced *Pseudomonas syringae* and *Xanthomonas axonopodis* genomes respectively. Sequence based search utilizing any other sequence alignment or repeat finding tools is also within scope of this disclosure. A relaxation of two mismatches was allowed to prevent false positives which could lead to over-prediction of possible targets. In this embodiment, nucleotide repeat sequences occurring more than 30 times at distant locations on the genome were considered. This number of occurrences may vary depending on the system requirements. If the number of times $R_n$ matches on the genomic sequences of strains of candidate pathogen genome/genomes is greater than the predefined threshold with a minimum value of 10, the sequence stretch is termed as target nucleotide repeat sequence. Although, the number of occurrences of the nucleotide repeat sequence might vary in different pathogens, a minimum of 10 occurrences is required for a nucleotide repeat sequence to be considered as a target sequence The dispersed nucleotide sequences at distant locations on the genome refers to stretches of nucleotide sequences which occur across the genome with a distance of predefined number of base pairs between them In one embodiment used in this disclosure the predefined number refers to a separation of >10000 base pairs between two nucleotide repeat sequences.

According to an embodiment of the disclosure, the processor 112 further includes the neighborhood gene identification module 116. The neighborhood gene identification module 116 is configured to identify a set of neighborhood genes present upstream and downstream of the set of nucleotide repeat sequences corresponding to the plant pathogen. On each plant pathogen genome (nucleotide sequence of the plant pathogen genome) where nucleotide repeat elements or their reverse complement occur, 10 flanking genes both upstream and downstream were found on each strand (+ and −) of DNA. The number of flanking genes considered may vary with the system.

According to an embodiment of the disclosure, the system 100 further includes the annotation module 118. The annotation module 118 categorizes or annotates the set of neighborhood genes based on their functional roles in the pathogen. Functional annotation of these genes was performed using HMM search with PFAM as the database. In other embodiments, databases like CDD, SMART etc. can be utilized. The use of any other methods such as PSSM, BLAST etc. is well within the scope of the disclosure.

These dispersed nucleotide repeat sequences RPSEUDO-S and RXAN at distant locations on the genome can be used as targets which can be further extended to target multiple flanking genes (which includes virulence and survival genes) simultaneously at distant multiple locations and carry out changes like but not limited to gene silencing, gene recombination, gene substitution with a new function etc. Functional categorization of these genes on the basis of pathways they are involved in was carried out using literature mining.

According to an embodiment of the disclosure, the system 100 further includes the testing module 120 and the administration module 122. The testing module 120 is configured to check the presence of secondary structure formation in the identified set of nucleotide repeat sequences. There could be the presence of the secondary structures such as hairpin loop formation. Depending on the presence of the secondary structure, the administration module 122 is configured to administer an engineered polynucleotide construct to treat the pathogenic infection. The construct works in such a way that it targets multiple regions in the genome simultaneously.

In an embodiment the construct may comprise of an engineered circular DNA comprising of an origin of replication. Further the construct may comprise of regulatory elements like a promoter sequence, ribosomal binding site, start codon, a cassette comprising of first and second enzyme flanking the nucleotide repeat sequence or its reverse complement of the nucleotide repeat sequence RPSEUDO-S/RXAN cloned into the system, stop codons and transcription terminator. The promoter sequence may depend on the pathogen being targeted as well as the regulation required to express the components of the construct at a specific targeted site. The construct may also be equipped to create a poly A tail in mRNA to stabilize the sequence. The poly A tail refers to a stretch of polynucleotide Adenine nucleotides at the 3' end of mRNA. In one embodiment, the first and second enzyme can be nickase and exonuclease cloned in any order. The target RPSEUDO-S/RXAN within the pathogen genome can be recognized and bound by the reverse complement sequence and the complex thus formed can be nicked by the nickase enzyme. The exonuclease can then chop of the duplex formed as well as flanking genes once it recognizes a nick. In another embodiment, the enzymes can be cas9 sequences (may be obtained from *Streptococcus pyogenes*) flanking the RPSEUDO-S/RXAN or the reverse complement of RPSEUDO-S/RXAN which can act as sgRNA (single guide RNA) for the CRISPR-Cas (Clustered Regularly Interspaced Short Palindromic Repeats) system hence obtained. The RPSEUDO-S/RXAN or its reverse complement is recognized by the reverse complement sequence or the target sequence on the polynucleotide construct and the is complex formed by the binding of RPSEUDO-S/RXAN sequence to its reverse complement. The cas9 may then act as an endonuclease and chop of the nick and flanking sequences. The nucleotide repeat sequence can be targeted by delivering an engineered polynucleotide construct using a bacterial, plasmid or a viral vector to the target bacterial cell. In one embodiment the composition may comprise of: the first element comprising a polynucleotide sequence of CRISPR-Cas system wherein the polynucleotide sequence may comprise a nucleotide repeat sequence (identified nucleotide repeat or its reverse complement) called a guide sequence capable of hybridizing to target sequence (nucleotide repeat sequence on pathogen), a tracr sequence and a tracr mate sequence. The second element may comprise of CRISPR enzyme coding sequences like CAS enzymes. It should be noted that in all these embodiments RPSEUDO-S/RXAN sequences can be cloned within same polynucleotide sequence along with a bacterial or viral vector and the other features mentioned above to target more than one pathogen using the same compact construct. Any other construct cassette that may bring about the recognition of the RPSEUDO-S/RXAN sequences in bacterial genomes and subsequent nicking and chopping of RPSEUDO-S/RXAN sequences and the flanking genes is within the scope of this invention.

In another embodiment, in addition to the above mentioned features, if bacterial conjugation is to be used as a construct delivery method, the construct may comprise of a relaxase, coding sequences for structural proteins (e.g. pili) and those for regulatory proteins for conjugation. It should be noted that in both embodiments multiple RPSEUDO-S/RXAN sequences can be cloned to target more than one pathogen using the same compact construct. Any other construct cassette that may bring about the recognition of the RPSEUDO-S/RXAN and subsequent chopping of RPSEUDO-S/RXAN and the flanking genes is within the scope of this invention. These polynucleotides comprising the nucleotide repeat sequence, the genes encoding enzymes and the other features discussed above can be inserted into laboratory acceptable vectors which allow insertion of external DNA fragments; In one embodiment construct may be carried by vectors like plasmid or phage based cloning vectors. The regulatory elements can be designed according to information available for the pathogen being targeted.

Figures 3, 3A, 3B:
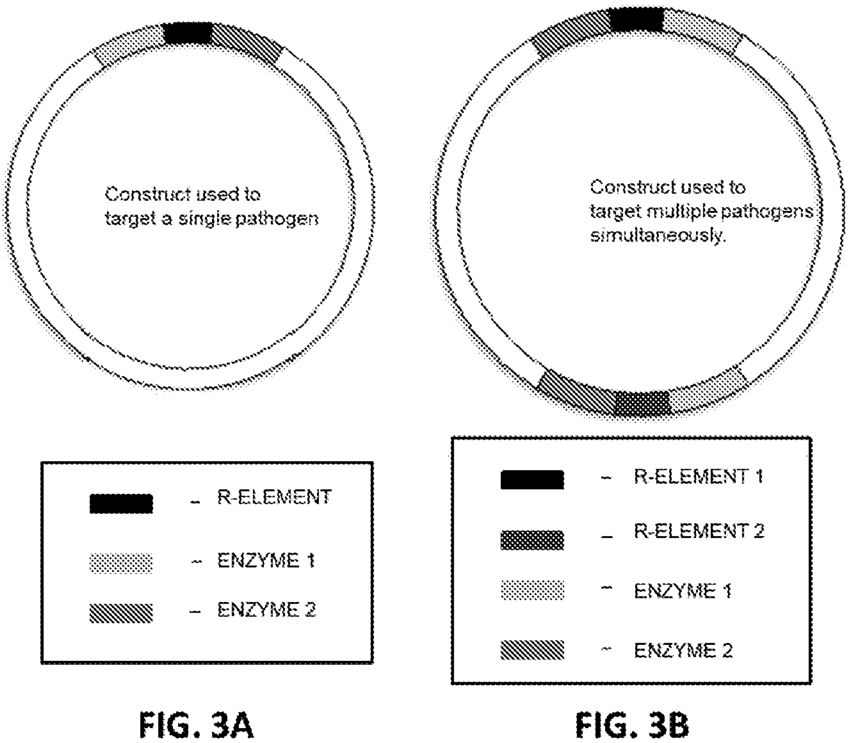
FIGS. 3A and 3B shows components of a construct containing multiple target sequences capable of combating one or more than one plant pathogenic infections respectively according to an embodiment of the disclosure.

In one embodiment, the construct may contain an enzyme 1, enzyme 2, identified nucleotide target sequence, R-element (RPSEUDO-S/RXAN) as shown in FIG. 3A. One of the enzyme 1 or enzyme 2 can be the nicking enzyme while the other will constitute nucleotide cleaving enzymes such as nuclease, exonuclease etc. Other enzymes with similar activities are also within scope of the invention. In another embodiment, the construct may be used to target multiple pathogens simultaneously as shown in FIG. 3B. The construct may contain repeat element 1 RPSEUDO-S and repeat element 2 RXAN cloned into one engineered polynucleotide along with enzyme 1 and enzyme 2.

Depending on the result of testing module 120, there could be two cases as follows:

Case I: If the identified nucleotide repeat sequences are found to be palindromic the following three strategies may be used.

Figure 4:
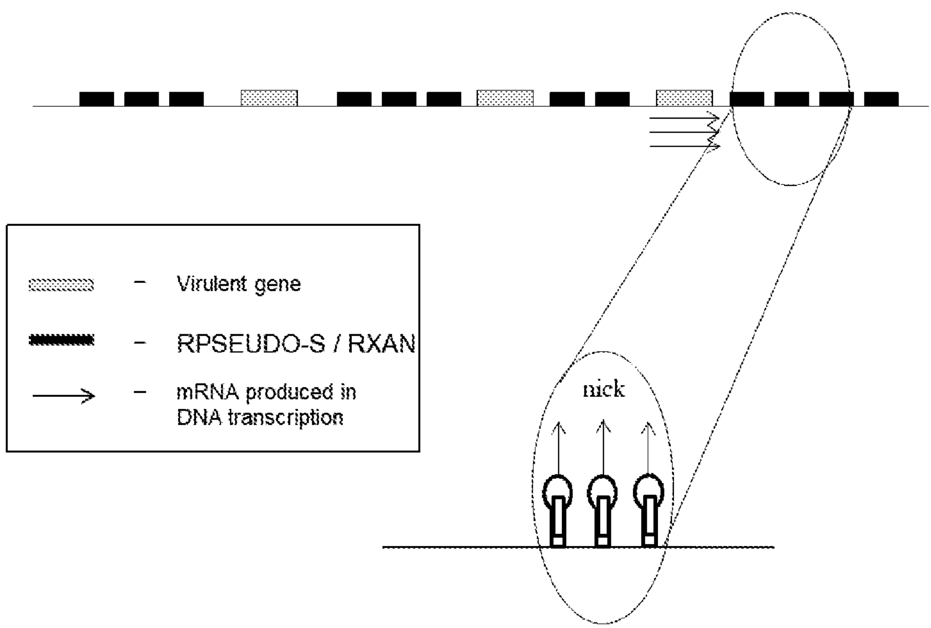
FIG. 4 shows targeting of palindromic and non-palindromic nucleotide repeat sequences in the genomes of plant pathogens *Pseudomonas syringae* and *Xanthomonas axonopodis* according to an embodiment of the disclosure.

Strategy I includes handling hairpin loops which hinders DNA transcription by stalling the RNA polymerase enzyme thereby down-regulating the flanking gene expression. In an embodiment, the strategy would involve use of the identified nucleotide repeat sequences as target and inserting a strong palindromic sequence to ensure the down-regulation of transcription of flanking genes Strategy II involves handling hairpin loops formed in the mRNA which could be involved in prevention of the early decay of mRNA thereby promoting the expression of important bacterial genes. In an embodiment, the strategy may include use of the identified nucleotide repeat sequences as target to nick the pathogen genome at multiple locations and cleave the flanking genes. In an example, a schematic representation of the *Pseudomonas syringae* and *Xanthomonas axonopodis* genomes showing nick of hairpins from RPSEUDO-S element and RXAN element respectively are shown in FIG. 4.

Strategy III is utilized if the identified nucleotide repeat sequences is found to be a transcription terminator and is followed by a polyA tail. In an embodiment, the identified nucleotide repeat sequence is used as target and a strong palindromic sequence is inserted to ensure that the transcriptional termination of the flanking genes occur and these genes are down-regulated in the pathogen.

Figure 5:
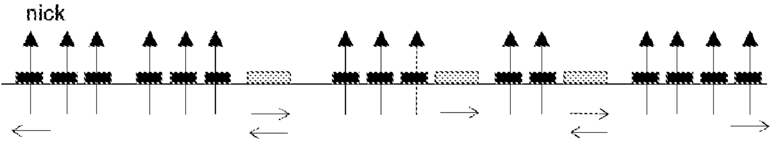
FIG. 5 shows enzymatic cleavage in the *Pseudomonas syringae* and *Xanthomonas axonopodis* genomes according to an embodiment of the disclosure.
Figure 5:
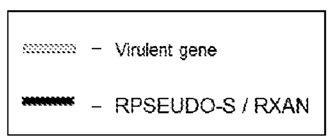

Case II: If the identified nucleotide repeat sequences are not found to be palindromic, the identified repeat sequences are used as target to nick the pathogen genome at multiple locations and cleave the flanking genes. A schematic representation of *Pseudomonas syringae* and *Xanthomonas axonopodis* genomes showing enzymatic cleavage in either directions is shown in FIG. 5.

In the present embodiment, the RPSEUDO-S sequence in *Pseudomonas syringae* and RXAN sequence in *Xanthomonas axonopodis*, which are used as example, are palindromic and may form a hairpin loop structure indicating their role in regulation of transcription. These loops may either form at DNA level or at the ends of their mRNA during DNA transcription. This hairpin loop in the mRNA could be involved in prevention of the early decay of mRNA, resulting in higher protein formation of the virulence genes which are in the vicinity of these palindromic elements. Reduction in pathogenicity can be achieved by decreasing the stability of mRNA corresponding to these virulent genes which can be attained by removing the hairpin loops. If hairpin loop formation takes place at DNA level it might regulate DNA supercoiling and concatenation. The hairpin loop is not followed by a polyA tail indicating it might not be working as transcription terminator.

The administration module 122 can use any pharmaceutically acceptable method of carrying the construct to target the conserved sequences in a pathogen genome. In different embodiments the utility can be, but not limited to oral medicine, topical creams, nasal administration, aerosol sprays, injectable cocktail etc.

In an embodiment, the construct can be administered to the infected site (either living beings or environmental site) through targeted construct delivery methods such as the use of targeted liposomes (wherein, the liposome is tagged on the external surface with molecules that may be specific and functionally important to the candidate genus and the tagged liposome can be used to transfer the construct into the pathogen), targeted nanoparticles wherein, a targeting molecule that is specific to the candidate genus can be attached to the nanoparticle along with the construct, thereby allowing the tagged nanoparticle (like but not limited to Ag or Au nanoparticle) to release the construct into the pathogen, phage based delivery method (wherein, the construct can be placed within the phage infecting the candidate genus thereby transferring the construct into pathogen) and bacterial conjugation (wherein, the construct can be placed in other bacteria that can conjugate with the candidate genus and the construct can be transferred to the pathogen through natural conjugation method) etc. In an embodiment, the lipid constitution of the membrane for the targeted liposome can be modified to target specific set of bacteria.

In another embodiment, immunoliposomes can be created with specific antibodies towards ligands of specific pathogen (for example, antibodies against concanavalin A for targeting extracellular matrix of biofilms). The lipid bilayer can be made sensitive to the toxins or other virulence factors of the pathogen in order to release the construct only in infected areas where toxins are present.

In another embodiment, the construct can also be administered to the infected site through non-targeted construct delivery methods such as the use of non-targeted nanoparticles (wherein, nanoparticles can form cages that can hold the construct which are then released into the pathogen), non-targeted liposomes (wherein, the liposomes are phospholipid capsules which can be used to hold the construct that can then merge with the pathogen cell membrane to release the construct inside the pathogen) etc. In an embodiment, attenuated bacteria can also be used to deliver nanoparticles into tissue spaces where they can be released to act upon actual site of infection (as shown in creation of NanoBEADS in a study where *Salmonella* was used to deliver nanoparticles containing a drug to deep tissues). In another example, minicells produced by bacteria can also be used to package the construct and deliver it to specific areas in the infected site. In another embodiment, these delivery methods can be used to target the construct to infected surfaces also. Any other laboratory accepted method of administration of the construct to the infected site is within the scope of this disclosure.

According to an embodiment of the disclosure, the efficacy module 124 is used to assess the efficacy of the treatment methodology described in this disclosure. The efficacy module 124 comprises of any laboratory acceptable methods of detecting presence of pathogens present at the infected site. In one embodiment, presence of viable living cells can be detected by utilizing presence of bacterial mRNA which has a short half-life and will not exist once the cells are dead. This mRNA based method may involve identifying antigen/protein specific for the pathogen which can be utilized as a marker for that pathogen and produced by the pathogen in abundance and the corresponding gene on the pathogen genome can be obtained. The mRNA corresponding to expression of these genes can be detected using techniques like but not limited to polymerase chain reaction (RT-PCR) assays or reverse transcriptase strand displacement amplification (RT-SDA) assays. In another embodiment, expression of proteins identified as specific to these pathogens can be detected using various laboratory accepted methods for protein purification and detection. Chromogenic enzyme assays for a pathogen are also within scope of the invention. Specific metabolites or compounds produced by a pathogen can also be detected (using different laboratory acceptable methods like Mass spectrometry, HPLC-MS, spectrometry-based methods etc.) to ascertain pathogen presence. In other embodiments, the identified antigens/marker sequences (e.g. sequence-characterized amplified region (SCAR) markers in *Xanthomonas axonopodis*) can be targeted using methods like nucleic acid amplification tests (NAAT), real time PCR, immunoassays (For example xcd108 antibody for *Xanthomonas axonopodis*) etc. as well as specific staining and microscopy techniques and flow cytometry methods of detecting pathogens are also within scope of this invention. PCR or Restriction Fragment Length Polymorphism (RFLP) based detection of 16S rRNA in order to identify pathogens can also be utilized. In one more embodiment, staining methods can also be utilized to identify a pathogen and establish viability of a pathogen cell (e.g. propidium iodide can be used for identifying dead cells). Cell toxicity assays can also be utilized for toxins based detection of pathogens. Further in case of sporulating bacteria, spore detection assays can also be utilized. In case of culturable bacteria, the viability of pathogens can even be established using culturing methods based on selective media followed by methods to detect specific pathogens discussed above. In another embodiment, the presence of pathogens can be estimated using phenotypic traits or symptoms of a disease. For example citrus canker often associated with presence of *P. syringae* can be determined by whitish or reddish exudates oozing on the trunks and branches, spots on leaves, browning of buds and flowers and misshapen fruits. Any other method of detecting pathogens are also within scope of this disclosure. In case pathogen presence is detected, the construct can be administered again using administration module 120 and repeated till pathogen is eliminated.

Figure 6A:
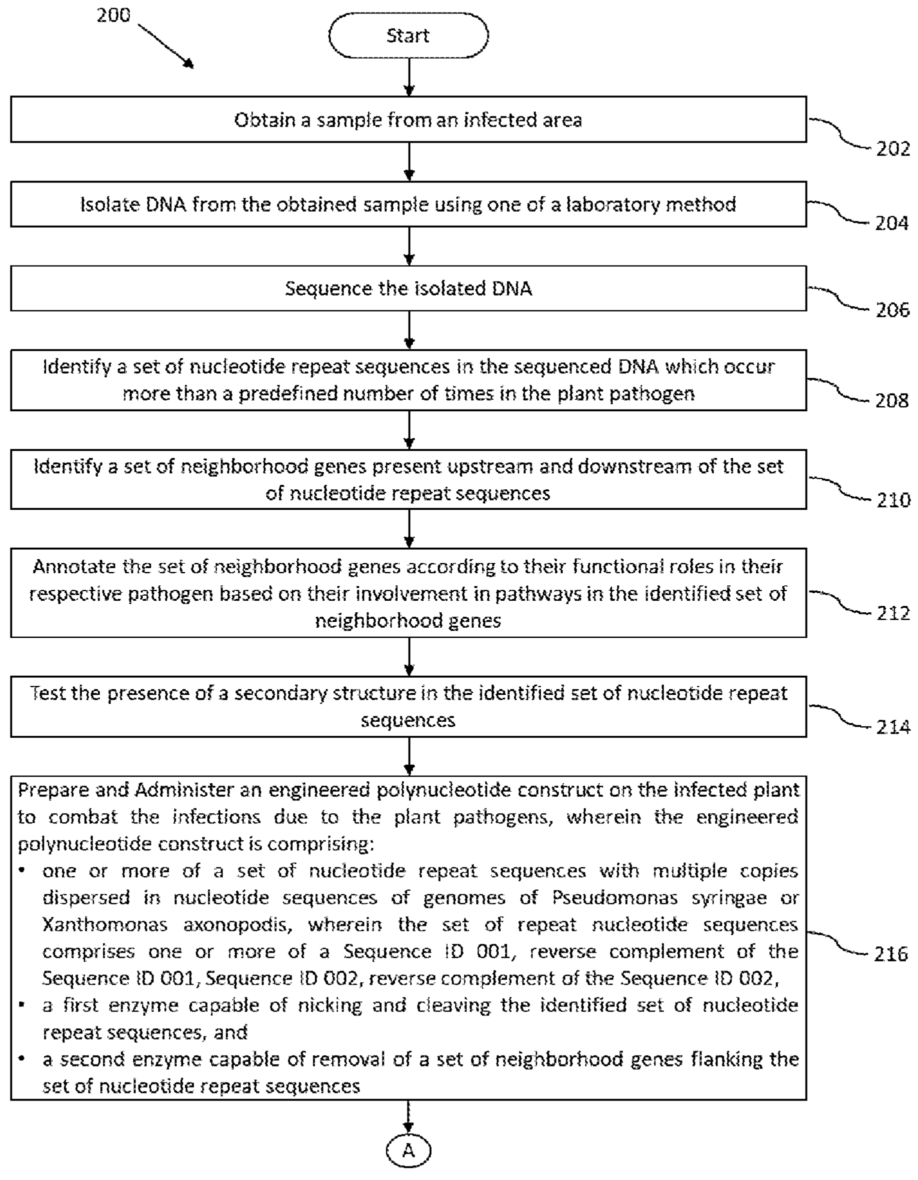
FIGS. 6A and 6B is a flowchart illustrating the steps involved in combating infections due to a plant pathogen according to an embodiment of the present disclosure.
Figure 6B:
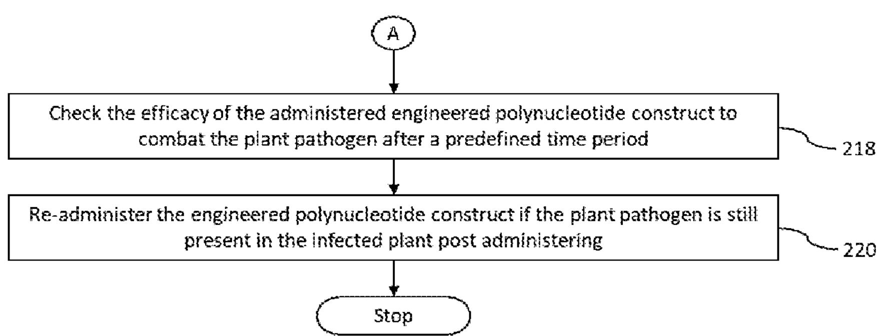

In operation, a flowchart 200 illustrating the steps involved for combating infections due to the plant pathogen can be shown in FIG. 6A-6B. Initially at 202, a sample is obtained from the infected plant. At step 204, DNA is extracted from the sample using the pathogen detection and DNA extraction module 106 which is also configured for pathogen detection. At step 206, the extracted DNA is sequenced using the sequencer 108. In the next step 208, the set of nucleotide repeat sequences in the extracted DNA or the repeats in the genome sequence of detected pathogen is identified which occur more than a predefined number of times (refers to the number of occurrences of nucleotide repeat sequence on a genome in a dispersed manner and this number might vary with system and pathogen under consideration where the minimum value of predefined number is 10) in the plant pathogen. In addition to that, the identified set of nucleotide repeat sequences are not specific to a single strain of the pathogen. In step 210, the set of neighborhood genes present upstream and downstream of the set of nucleotide repeat sequences was identified. In step 212, the set of neighborhood genes is categorized or annotated according to functional roles of each of neighborhood gene in the plant pathogen. At step 214, the presence of the secondary structure is tested in the set of nucleotide repeat sequences. The set of nucleotide repeat sequences may be palindromic in nature which may result in the formation of hairpin loops istration module can be utilized repetitively till the plant pathogen is eliminated from the site. And finally at step 220, the engineered polynucleotide construct is re-administered if the plant pathogen is still present after checking using efficacy module in the infected plant.

According to an embodiment of the disclosure, the system 100 can also be used in combination with various other known methods to effectively treat the plant pathogenic infection. The disclosure may be used in combination with various other prior arts to form an effective strategy for preventive and therapeutic measures. In an embodiment, as a preventive measure the disclosure can be used in combination with various other antibacterial agents. In another embodiment, the quorum quenchers can be used along with the invention to tackle the biofilm formation. As a therapeutic measure the disclosure can be used in combination with various other antimicrobial methods. In another embodiment, the invention can be used along with antibiotic sprays.

According to an embodiment of the disclosure, the system 100 for combating infections due to *Pseudomonas syringae* and *Xanthomonas axonopodis* can also be explained with the help of following example for *Pseudomonas syringae* and *Xanthomonas axonopodis*.

Nucleotide repeat elements were identified on the sequenced genomes of *Pseudomonas syringae* and *Xanthomonas axonopodis* by taking a sequence stretch of predefined length Rn and searching across the genome for similar sequence stretches as done by several alignment software. In this embodiment, PILER software was used. The identified consensus nucleotide repeat sequences for both the pathogens are shown below.

Sequence 001: *Pseudomonas syringae*:
GGACGC[G|A]GAGCGTCC[A|G]GAACGGCATGN$_{(0-1)}$CGACGC

[A|G]GAGCGTCGCACGATA

Sequence 002: *Xanthomonas axonopodis*:
G[G|A]CGGC[A|G]TCCATG[C|T]CGNCA

At step 216, an engineered polynucleotide construct is prepared and administered on the infected plant to combat the infections due to the plant pathogen, wherein the engineered polynucleotide construct is comprising:

- one or more of the set of nucleotide repeat sequences with multiple copies dispersed in nucleotide sequences of genomes of *Pseudomonas syringae* or *Xanthomonas axonopodis*, wherein the set of nucleotide repeat sequences comprises one or more of a Sequence ID 001, reverse complement of the Sequence ID 001, Sequence ID 002, reverse complement of the Sequence ID 002.
- a first enzyme capable of nicking and cleaving the identified set of nucleotide repeat sequences, and
- a second enzyme capable of removal of a set of neighborhood genes flanking the set of nucleotide repeat sequences. In another example the first enzyme is a nicking enzyme and the second enzyme is a cleaving enzyme The administration of construct aims at targeting the set of identified nucleotide repeats and removal of flanking genes on genomes of the plant pathogen infecting the area. The construct works in such a way that it targets multiple regions in the pathogenic genome simultaneously. At step 218, the efficacy of the administration module is assessed and in case the plant pathogen presence is detected at the site, admin- On further analysis as discussed below, it was observed that these conserved stretches (as discussed above) are found in the vicinity of highly virulent and, certain essential genes of both *Pseudomonas syringae* and *Xanthomonas axonopodis*. Results of sequence similarity analysis (using BLAST in this embodiment) revealed that these sequences doesn't show any significant sequence similarity in any other bacterial genus and on the host genome reducing the possibility of a cross-reactivity. Hence, these elements are ideal candidates for targeting pathogenic AMR *Pseudomonas syringae* and *Xanthomonas axonopodis*.

In the first step as mentioned above nucleotide sequence stretches RPSEUDO-S and RXAN which repeat multiple times on *Pseudomonas syringae* and *Xanthomonas axonopodis* genomes respectively were identified.

Conserved nucleotide repeat elements were identified on *Pseudomonas syringae* and *Xanthomonas axonopodis* genomes by taking sequence stretches of predefined length Rn (50-70 for *Pseudomonas syringae* and 30-50 for *Xanthomonas axonopodis* in this embodiment), keeping the difference in the start position of $R_{ni+1}$ and $R_{ni}$ as 5 nucleotides. The number of times the element RPSEUDO-S and RXAN occur on the nucleotide sequence of genomes of strains of these pathogens (sequenced and deposited in NCBI genomes repository) have been given below along with the positions of occurrence of nucleotide repeats on the genome

*Xanthomonas axonopodis* sequenced strains are as follows:

*Xanthomonas*_axonopodis_pv._citri_str._306_-_GCA_000007165.1_ASM716v1

Number of occurrences: 21

(351999,352018), (970374,970393), (1178280,1178299), (1297326,129734 5), (1708828,1708847), (1709058, 1709077), (2314630,2314649), (2380452,238047 1), (2894078,2894097), (2991537,2991556), (2991712, 2991731), (3382830,338284 9), (3976811,3976830), (3977036,3977055), (4020462,4020481), (4134937, 413495 6), (4220481,4220500), (4373913,4373932), (4726072,4726091), (4773185,477320 4), (4981921, 4981940)

*Xanthomonas*_axonopodis_pv._citrumelo_F1_-_GCA_000225915.1_ASM22591v1

Number of occurrences: 23

(110136,110155), (110313,110332), (710018,710037), (1119718,1119737), (1650873,1650892), (2165397, 2165416), (2165581,2165600), (2282313,2282332), (3251858,3251877), (3323461,3323480), (3550486, 3550505), (3843033,3843052), (4030468,4030487), (4048109,4048128), (4048333,4048352), (4130283, 4130302), (4179880,4179899), (4472894,4472913), (4569214,4569233), (4569391,4569410), (4671641, 4671660), (4671814,4671833), (4760129,4760148)

*Xanthomonas*_axonopodis_Xac29-1_-_GCA_000348585.1_ASM34858v1

Number of occurrences: 24

(353210,353229), (974307,974326), (1182389,1182408), (1301072,130109 1), (1711440,1711459), (1711480, 1711499), (1711710,1711729), (2205015,220503 4), (2205189,2205208), (2327012,2327031), (2393412, 2393431), (2909673,290969 2), (3007310,3007329), (3007485,3007504), (3398214,3398233), (3985126, 398514 5), (3985351,3985370), (4028788,4028807), (4143231,4143250), (4228778,422879 7), (4382217, 4382236), (4705336,4705355), (4752376,4752395), (4961589,496160 8)

*Pseudomonas syringae* sequenced strains are as follows:

*Pseudomonas*_syringae_CC1557_-_GCA_000452705.3_ASM45270v3

Number of occurrences: 11

[(32598, 32647), (241272, 241321), (368533, 368582), (852115, 852164), (1453848, 1453896), (1597124, 1597173), (3800879, 3800928), (4592566, 4592615), (5244284, 5244333), (5282219, 5282268), (5497075, 5497124)]

*Pseudomonas*_syringae_pv._actinidiae_-_GCA_001913215.1_ASM191321v1

Number of occurrences: 62

[(148565, 148613), (148861, 148909), (149009, 149057), (214089, 214137), (445999, 446047), (454977, 455025), (824271, 824319), (930502, 930551), (1325265, 1325313), (1480790, 1480839), (1976010, 1976058), (1997128, 1997176), (1997497, 1997545), (1997611, 1997660), (1997726, 1997774), (1997955, 1998003), (2086601, 2086649), (2152468, 2152516), (2160231, 2160279), (2261330, 2261378), (2531655, 2531703), (2649091, 2649139), (2705508, 2705556), (2710063, 2710111), (2723781, 2723829), (2856845, 2856893), (2857186, 2857234), (2887823, 2887871), (3111341, 3111389), (3207853, 3207901), (3268795, 3268844), (3940529, 3940577), (4052469, 4052517), (4101126, 4101174), (4152712, 4152760), (4153339, 4153387), (4421519, 4421567), (4486305, 4486354), (4643399, 4643447), (4667097, 4667145), (4760798, 4760847), (4869321, 4869369), (4869689, 4869737), (4881620, 4881668), (5422304, 5422353), (5422515, 5422564), (5422704, 5422753), (5687419, 5687467), (5731034, 5731082), (5731193, 5731241), (5747651, 5747699), (5970016, 5970065), (5999334, 5999382), (6079651, 6079699), (6079841, 6079889), (6101906, 6101954), (6102030, 6102078), (6169631, 6169679), (6227978, 6228026), (6262443, 6262492), (6307783, 6307831), (6485856, 6485904)]

*Pseudomonas*_syringae_pv._actinidiae_-_GCA_001913235.1_ASM191323v1

Number of occurrences: 62

[(148565, 148613), (148861, 148909), (149009, 149057), (214089, 214137), (445998, 446046), (454976, 455024), (824271, 824319), (930502, 930551), (1325266, 1325314), (1480791, 1480840), (1875159, 1875207), (1896277, 1896325), (1896646, 1896694), (1896760, 1896809), (1896875, 1896923), (1897104, 1897152), (1985750, 1985798), (2051617, 2051665), (2059380, 2059428), (2160479, 2160527), (2430804, 2430852), (2548240, 2548288), (2604657, 2604705), (2609213, 2609261), (2622931, 2622979), (2755995, 2756043), (2756336, 2756384), (2786973, 2787021), (3010491, 3010539), (3107003, 3107051), (3167945, 3167994), (3837848, 3837896), (3949788, 3949836), (3998443, 3998491), (4050029, 4050077), (4050656, 4050704), (4318836, 4318884), (4383622, 4383671), (4540716, 4540764), (4564414, 4564462), (4658115, 4658164), (4766638, 4766686), (4767006, 4767054), (4778937, 4778985), (5319622, 5319671), (5319833, 5319882), (5320022, 5320071), (5568297, 5568345), (5611912, 5611960), (5612071, 5612119), (5628529, 5628577), (5850894, 5850943), (5880212, 5880260), (5960529, 5960577), (5960719, 5960767), (5982784, 5982832), (5982908, 5982956), (6050509, 6050557), (6108856, 6108904), (6143321, 6143370), (6188661, 6188709), (6366735, 6366783)]

*Pseudomonas*_syringae_pv._actinidiae_-_GCA_002024285.1_ASM202428v1

Number of occurrences: 62

[(148561, 148609), (148857, 148905), (149005, 149053), (214085, 214133), (445996, 446044), (454974, 455022), (824270, 824318), (930501, 930550), (1327133, 1327181), (1484329, 1484378), (1971154, 1971202), (1992272, 1992320), (1992641, 1992689), (1992755, 1992804), (1992870, 1992918), (1993099, 1993147), (2081745, 2081793), (2147612, 2147660), (2155363, 2155411), (2256462, 2256510), (2526787, 2526835), (2644245, 2644293), (2700662, 2700710), (2705218, 2705266), (2718936, 2718984), (2852000, 2852048), (2852341, 2852389), (2882978, 2883026), (3106496, 3106544), (3203008, 3203056), (3263950, 3263999), (3932681, 3932729), (4044621, 4044669), (4093276, 4093324), (4144862, 4144910), (4145489, 4145537), (4413669, 4413717), (4478455, 4478504), (4634650, 4634698), (4658348, 4658396), (4752049, 4752098), (4860516, 4860564), (4860884, 4860932), (4872815, 4872863), (5413500, 5413549), (5413711, 5413760), (5413900, 5413949), (5570982, 5571030), (5614597, 5614645), (5614756, 5614804), (5631214, 5631262), (5851722, 5851771), (5881040, 5881088), (5961357, 5961405), (5961547, 5961595), (5983612, 5983660), (5983736, 5983784), (6051321, 6051369), (6109668, 6109716), (6144133, 6144182), (6189473, 6189521), (6367547, 6367595)]

*Pseudomonas*_syringae_pv._actinidiae_-_GCA_002024305.1_ASM202430v1
Number of occurrences: 62
[(148561, 148609), (148857, 148905), (149005, 149053), (214085, 214133), (445996, 446044), (454974, 455022), (824270, 824318), (930501, 930550), (1327133, 1327181), (1482658, 1482707), (1927156, 1927205), (1927345, 1927394), (1927556, 1927605), (2468242, 2468290), (2480173, 2480221), (2480541, 2480589), (2589007, 2589056), (2682709, 2682757), (2706407, 2706455), (2863500, 2863549), (2928287, 2928335), (3196466, 3196514), (3197093, 3197141), (3248679, 3248727), (3297334, 3297382), (3409274, 3409322), (4078004, 4078053), (4138947, 4138995), (4235459, 4235507), (4458977, 4459025), (4489614, 4489662), (4489955, 4490003), (4623019, 4623067), (4636737, 4636785), (4641293, 4641341), (4697710, 4697758), (4815168, 4815216), (5085493, 5085541), (5186592, 5186640), (5194343, 5194391), (5261464, 5261512), (5350110, 5350158), (5350339, 5350387), (5350453, 5350502), (5350568, 5350616), (5350937, 5350985), (5372055, 5372103), (5571461, 5571509), (5615076, 5615124), (5615235, 5615283), (5631693, 5631741), (5852201, 5852250), (5881519, 5881567), (5961836, 5961884), (5962026, 5962074), (5984091, 5984139), (5984215, 5984263), (6051800, 6051848), (6110147, 6110195), (6144612, 6144661), (6189952, 6190000), (6368026, 6368074)]
*Pseudomonas*_syringae_pv._actinidiae_ICMP_18708_-_GCA_000344355.2_ASM34435v2
Number of occurrences: 62
[(148565, 148613), (148861, 148909), (149009, 149057), (214089, 214137), (445999, 446047), (454977, 455025), (824273, 824321), (930504, 930553), (1325269, 1325317), (1480794, 1480843), (1875162, 1875210), (1896280, 1896328), (1896649, 1896697), (1896763, 1896812), (1896878, 1896926), (1897107, 1897155), (1985753, 1985801), (2051620, 2051668), (2059383, 2059431), (2160482, 2160530), (2430807, 2430855), (2548243, 2548291), (2604660, 2604708), (2609216, 2609264), (2622934, 2622982), (2755998, 2756046), (2756339, 2756387), (2786976, 2787024), (3010494, 3010542), (3107006, 3107054), (3167948, 3167997), (3837851, 3837899), (3949791, 3949839), (3998446, 3998494), (4050032, 4050080), (4050659, 4050707), (4318839, 4318887), (4383625, 4383674), (4540719, 4540767), (4564417, 4564465), (4658118, 4658167), (4766641, 4766689), (4767009, 4767057), (4778940, 4778988), (5319625, 5319674), (5319836, 5319885), (5320025, 5320074), (5577958, 5578006), (5621573, 5621621), (5621732, 5621780), (5638190, 5638238), (5860555, 5860604), (5889873, 5889921), (5970190, 5970238), (5970380, 5970428), (5992445, 5992493), (5992569, 5992617), (6060170, 6060218), (6118517, 6118565), (6152982, 6153031), (6198322, 6198370), (6376396, 6376444)]
*Pseudomonas*_syringae_pv._actinidiae_ICMP_18884_-_GCA_000648735.3_ASM64873v3
Number of occurrences: 62
[(148565, 148613), (148861, 148909), (149009, 149057), (214089, 214137), (445998, 446046), (454976, 455024), (824271, 824319), (930502, 930551), (1325266, 1325314), (1480791, 1480840), (1875159, 1875207), (1896277, 1896325), (1896646, 1896694), (1896760, 1896809), (1896875, 1896923), (1897104, 1897152), (1985750, 1985798), (2051617, 2051665), (2059380, 2059428), (2160479, 2160527), (2430804, 2430852), (2548240, 2548288), (2604657, 2604705), (2609213, 2609261), (2622931, 2622979), (2755995, 2756043), (2756336, 2756384), (2786973, 2787021), (3010491, 3010539), (3107003, 3107051), (3167945, 3167994), (3837848, 3837896), (3949788, 3949836), (3998443, 3998491), (4050029, 4050077), (4050656, 4050704), (4318836, 4318884), (4383622, 4383671), (4540716, 4540764), (4564414, 4564462), (4658115, 4658164), (4766638, 4766686), (4767006, 4767054), (4778937, 4778985), (5319622, 5319671), (5319833, 5319882), (5320022, 5320071), (5577956, 5578004), (5621571, 5621619), (5621730, 5621778), (5638188, 5638236), (5860553, 5860602), (5889871, 5889919), (5970188, 5970236), (5970378, 5970426), (5992443, 5992491), (5992567, 5992615), (6060168, 6060216), (6118515, 6118563), (6152980, 6153029), (6198320, 6198368), (6376394, 6376442)]
*Pseudomonas*_syringae_pv._actinidiae_ICMP_9853_-_GCA_000344335.2_ASM34433v2
Number of occurrences: 58
[(66144, 66192), (66431, 66479), (119170, 119218), (189149, 189197), (189303, 189351), (198276, 198324), (226236, 226285), (687602, 687651), (777612, 777660), (777736, 777784), (799801, 799849), (799991, 800039), (852313, 852362), (925650, 925699), (925861, 925910), (926050, 926099), (1338897, 1338945), (1537886, 1537934), (1548153, 1548201), (2003315, 2003363), (2232197, 2232245), (2309388, 2309437), (2394580, 2394628), (2622344, 2622392), (2933784, 2933832), (3286037, 3286085), (3288223, 3288271), (3306352, 3306400), (3322151, 3322199), (3426666, 3426714), (3428769, 3428817), (3429110, 3429158), (3764094, 3764142), (3778796, 3778844), (3779176, 3779224), (3824150, 3824198), (3824777, 3824825), (3952252, 3952300), (4136990, 4137038), (4244061, 4244109), (4244185, 4244233), (4252661, 4252709), (4625125, 4625173), (4625354, 4625402), (4697901, 4697949), (4721484, 4721532), (4825051, 4825100), (4897404, 4897453), (5050137, 5050185), (5050489, 5050537), (5459107, 5459155), (5459443, 5459491), (5734113, 5734161), (5750732, 5750780), (5882698, 5882746), (5974292, 5974340), (6200981, 6201029), (6314277, 6314325)]
*Pseudomonas*_syringae_pv._syringae_B301D_-_GCA_000988485.1_ASM98848v1
Number of occurrences: 18
[(405972, 406020), (524122, 524170), (735729, 735778), (1146615, 1146663), (1146747, 1146795), (1254020, 1254069), (1982767, 1982816), (1982911, 1982960), (2142519, 2142568), (2142667, 2142716), (2142816, 2142865), (2190483, 2190531), (2190638, 2190686), (4344901, 4344949), (4422681, 4422730), (4439551, 4439599), (5425072, 5425120), (6038400, 6038448)]
*Pseudomonas*_syringae_pv._syringae_B728a_-_GCA_000012245.1_ASM1224v1
Number of occurrences: 23
[(461329, 461377), (672756, 672805), (1117633, 1117681), (1226194, 1226243), (1226412, 1226461), (2084831, 2084880), (2084977, 2085026), (2085122, 2085171), (2232684, 2232733), (2232833, 2232882), (2232981, 2233030), (2233129, 2233178), (2233277, 2233326), (2280831, 2280879), (2280986, 2281034), (4389313, 4389361), (4398747, 4398795), (4470479, 4470528), (5464389, 5464437), (5464561, 5464609), (5464734, 5464782), (5466304, 5466352), (6042574, 6042622)]

*Pseudomonas*_syringae_pv._tomato_str._DC3000_-_GCA_000007805.1_ASM780v1
Number of occurrences: 44
[(102566, 102615), (140979, 141027), (249188, 249236), (423425, 423473), (458722, 458771), (484635, 484683), (492860, 492908), (889356, 889404), (998752, 998801), (1388074, 1388122), (1531696, 1531745), (2063542, 2063590), (2063666, 2063714), (2063790, 2063838), (2322761, 2322810), (2490263, 2490312), (2514493, 2514541), (2721931, 2721979), (3312058, 3312106), (3312425, 3312473), (3685837, 3685885), (3970609, 3970657), (4153551, 4153599), (4302777, 4302825), (4599007, 4599055), (4599190, 4599238), (4616192, 4616240), (4651099, 4651147), (4728565, 4728613), (5258709, 5258757), (5259045, 5259093), (5259381, 5259429), (5560859, 5560907), (5743217, 5743266), (5748113, 5748161), (5770625, 5770673), (5887299, 5887347), (5967418, 5967466), (6008949, 6008998), (6021465, 6021514), (6045706, 6045754), (6258849, 6258897), (6273753, 6273802), (6275343, 6275392)]
*Pseudomonas*_syringae_UMAF0158_-_GCA_001281365.1_ASM128136v1
Number of occurrences: 13
[(1894028, 1894077), (2159975, 2160023), (3265059, 3265107), (3664762, 3664810), (3742845, 3742893), (4039204, 4039252), (4789040, 4789088), (4857894, 4857943), (4895698, 4895747), (4896053, 4896101), (5589647, 5589696), (5740591, 5740640), (5740703, 5740752)]

In this implementation, stretches of both the identified sequences RPSEUDO-S and RXAN were aligned within the genome by local alignment (as implemented in PILER software) to find the location of these elements in all sequenced *Pseudomonas syringae* and *Xanthomonas axonopodis* genomes respectively. Sequence based search utilizing any other alignment or repeat finding tools can also be utilized for this purpose.

In the second step, identification and annotation of gene neighborhood of repeat elements was performed.

On each of the *Pseudomonas syringae* and *Xanthomonas axonopodis* genomes where nucleotide repeat elements RPSEUDO-S and RXAN occur respectively, 10 flanking genes both upstream and downstream were found on each strand (+10 and −10) of DNA. Functional annotation of these genes was performed using HMM search with PFAM as the database. In other embodiments, databases like CDD, SMART etc. can be utilized. Functional categorization of these genes on the basis of pathways they are involved in was carried out using literature mining. The broad categories of the same have been provided in Table 1 and Table 2,

TABLE 1

Summary of proteins in vicinity of conserved sequence RPSEUDO-S repeat in *Pseudomonas syringae* genome.

| Category | Genes | Function |
|---|---|---|
| | Pathogenic/Virulence proteins | |
| Toxin | Type IV pilius protein cluster PilQ/J/R/S/B/C | Plays major role in motility and virulence of the pathogen |
| | FimA | Type I fimbrial protein essential for virulence |
| Competence proteins | ComL | Involved in uptake of exogenous DNA |

TABLE 1-continued

Summary of proteins in vicinity of conserved sequence RPSEUDO-S repeat in *Pseudomonas syringae* genome.

| Category | Genes | Function |
|---|---|---|
| | Survival Proteins | |
| Stress Response | TauD | Pyoverdine biosynthesis-essential to survive under iron limiting conditions |
| | Ter B/C/D/E | Tellurium resistance cluster |
| | USP | Universal stress response protein |
| DNA Repair machinery | Uvr_D helicase | Excision repair proteins |
| | DNA Topoisomerase I | Unwinds negative supercoiling |
| | RadC | Double stranded DNA repair |
| | Rnase_T (exonuclease) | Involved in DNA repair |
| | Essential Proteins | |
| Essential Proteins | DNA polymerase III | Involved in DNA synthesis |
| | tRNA-synthase | Involved in production of tRNA |
| | transketolase | Essential in pentose phosphate pathway |
| | Transporters | Uptake of glucose and other carbohydrate sources by the bacteria as well as transport of other essential components across the bacterial cell. |
| | MbtH | Important in tyrosine adenylation activity |
| | OprD | Outer membrane porin protein, essential for cell permeability |

TABLE 2

Summary of proteins in vicinity of conserved sequence RXAN repeat in *Xanthomonas axonopodis* genome.

| Category | Genes | Function |
|---|---|---|
| | Pathogenic/Virulence Proteins | |
| Toxin | Flagellar basal body protein FlgG/A/I | Plays major role in motility and virulence of the pathogen |
| | Type IV pilius assembly proteins PilZ | Plays major role in motility and virulence of the pathogen |
| | Survival Proteins | |
| Competence proteins | ComE | Involved in uptake of exogenous DNA |
| Stress Response | BatD | Oxygen tolerance protein |
| | CopA/B | Copper resistance protein |
| | USP | Universal stress response protein |
| | OsmC | Osmotically inducible stress-induced protein |
| DNA Repair machinery | Uvr_D helicase | Excision repair proteins |
| | PmbA_TldD | Modulator of DNA gyrase protein |
| | RecJ (exonuclease) | Involved in single stranded DNA break repair |
| | Endonuclease_N S | DNA/RNA non-specific endonuclease |

TABLE 2-continued

Summary of proteins in vicinity of conserved sequence RXAN repeat in *Xanthomonas axonopodis* genome.

| Category | Genes | Function |
|---|---|---|
| Essential Proteins | | |
| Essential Proteins | DNA polymerase III | Involved in DNA synthesis |
| | tRNA-synthase | Involved in production of tRNA |
| | CheW | Involved in relay of chemotaxis signaling, especially in flagellar movement |
| | Transporters | Uptake of glucose and other carbohydrate sources by the bacteria as well as transport of other essential components across the bacterial cell. |

TABLE 2-continued

Summary of proteins in vicinity of conserved sequence RXAN repeat in *Xanthomonas axonopodis* genome.

| Category | Genes | Function |
|---|---|---|
| | flavoprotein-ubiquinone oxidoreductase | Essential for electron transfer in the bacterial membrane |
| | acyl-CoA dehydrogenase | Essential enzyme for the fatty acid metabolism |

In the third step, the nucleotide repeat element sequence near the pathogenic regions were targeted. The identified repeat sequences were then checked for potential secondary structure formation such as hairpin loops. It is seen that both of these consensus repeat sequence stretches RPSEUDO-S and RXAN do form a potential hairpin loop.

The RPSEUDO-S and RXAN element nucleotide repeat sequences are palindromic and may form a hairpin loop structure indicating their role in regulation of transcription. These loops may either form at DNA level or at the ends of their mRNA during DNA transcription. These hairpin loops in the mRNA could be involved in prevention of the early decay of mRNA, resulting in higher protein formation of the virulence genes which are in the vicinity of these palindromic elements. Reduction in pathogenicity can be achieved by decreasing the stability of mRNA corresponding to these virulent genes which can be attained by removing the hairpin loops. If hairpin loop formation takes place at DNA level it might regulate DNA supercoiling. The hairpin loops are not followed by a polyA tail and hence may not act as transcription terminator.

The repeat sequences RPSEUDO-S and RXAN discussed above can be targeted using various laboratory accepted methods. One possible strategy is as follows. A construct containing target sequence, an enzyme capable of cutting at the region where target sequence binds (nickase in one embodiment) and an capable of recognizing the nick and chopping off flanking regions (exonuclease in one embodiment).

And finally in the fourth step, a preventive and therapeutic strategy was used. The disclosure may be used in combination with various other prior arts to form an effective strategy for preventive and therapeutic measures. As a preventive measure the invention can be used in combination with various other antibacterial agents. One implementation would be the use of quorum quenchers along with the invention to tackle the biofilm formation. As a therapeutic measure the invention can be used in combination with various other antimicrobial methods. One implementation would be to use this invention along with antibiotic sprays.

The embodiments of present disclosure herein provides the method and system for combating infections due to plant pathogens Sequences and their reverse complements have been disclosed Sequence 001: *Pseudomonas syringae*:
GGACGC[G|A]GAGCGTCC[A|G]GAACGGCATGN$_{(0-1)}$CGACGC

[A|G]GAGCGTCGCACGATA

Sequence 002: *Xanthomonas axonopodis*:
G[G|A]CGGC[A|G]TCCATG[C|T]CGNCA where N refers to any nucleotide out of A, T, G and C and numeric values in subscripts indicate the range of the number of times a nucleotide or a set of nucleotides is repeated in the sequence.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein address unresolved problem associated with the plant pathogens such as biofilm formation. The embodiment provides a system and method for combating infections due to plant pathogens.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

The invention claimed is:

1. A method for combating infections due to a plant pathogen, the method comprising:
- obtaining a sample from an infected plant;
- isolating and extracting DNA from the obtained sample using one of laboratory methods;
- sequencing the isolated DNA to get a characterized sample using a sequencer;
- identifying, via one or more hardware processors, a set of nucleotide repeat sequences in the sequenced DNA which occur more than a predefined number of times in the plant pathogen;
- identifying, via the one or more hardware processors, a set of neighborhood genes present upstream and downstream of the set of nucleotide repeat sequences;
- annotating, via the one or more hardware processors, the set of neighborhood genes according to their functional roles in their respective pathogen based on their involvement in pathways in the identified set of neighborhood genes;

testing, via the one or more hardware processors, presence of a secondary structure in the identified set of nucleotide repeat sequences;

preparing and administering an engineered polynucleotide construct on the infected plant to combat the infections due to the plant pathogen, wherein the engineered polynucleotide construct comprising:

one or more of the set of nucleotide repeat sequences with multiple copies dispersed in nucleotide sequences of genomes of *Pseudomonas syringae* or *Xanthomonas axonopodis*, wherein the set of nucleotide repeat sequences comprises one or more of a Sequence ID 001, reverse complement of the Sequence ID 001, Sequence ID 002, reverse complement of the Sequence ID 002, a first enzyme capable of nicking and cleaving the identified set of nucleotide repeat sequences, and a second enzyme capable of removal of a set of neighborhood genes flanking the set of nucleotide repeat sequences, checking the efficacy of the administered engineered polynucleotide construct to combat the plant pathogen after a predefined time period, and re-administering the engineered polynucleotide construct if the plant pathogen is still present in the infected plant post administering.

2. The method according to claim 1 wherein the DNA isolation methods comprise of laboratory standardized protocols including miniprep DNA extraction kits.

3. The method according to claim 1, wherein the sample is collected from the whole plant or part of plant comprising root, stem, leaf, seeds, fruits, or the soil samples around the root zone in and around the infected root of the plant to identify the disease pathogen.

4. The method according to claim 1 wherein the plurality of pathogen detection method comprises one or more of:

a sequencing technique, a flow cytometry based methodology, a microscopic examination of the microbes in collected sample, a microbial culture of pathogens in vitro, immunoassays, cell toxicity assay, enzymatic, colorimetric or fluorescence assays, assays involving spectroscopic/spectrometric/chromatographic identification and screening of signals from complex microbial populations.

5. The method according to claim 1, wherein the pathogen detection may also comprise of one or more of sequenced microbial DNA data, a microscopic imaging data, a flow cytometry cellular measurement data, a colony count and cellular phenotypic data of microbes grown in in-vitro cultures, immunological data, proteomic/metabolomics data, and a signal intensity data.

6. The method according to claim 1 further comprising sequenced microbial data, wherein the sequenced microbial data comprises sequences obtained from sequencing platforms comprising sequences of marker genes including 16S rRNA, Whole Genome Shotgun (WGS) sequences, sequences obtained from a fragment library based sequencing technique, sequences from a mate-pair library or a paired-end library based sequencing technique, or a combination thereof.

7. The method according to claim 1, wherein the polynucleotides are inserted into vectors which allow insertion of external DNA fragments, wherein the engineered polynucleotide construct is carried by plasmid or phage based cloning vectors, wherein the engineered polynucleotide construct further comprises bacteria specific promoter sequence, a terminator sequence, a stretch of Thymine nucleotides which is transcribed into a polyA tail for stabilizing the mRNAs transcripts corresponding to each enzyme, wherein the promoters and terminators specific to candidate bacteria can be utilized in the construct.

8. The method according to claim 1 wherein the engineered polynucleotide construct comprises of a CRISPR-Cas system, comprising:

a CRISPR enzyme, a guide sequence capable of hybridizing to the identified target nucleotide repeat sequence within the pathogen genome, a tracr mate sequence, and a tracr sequence, wherein the guide sequence, the tracr mate and the tracr sequences are linked to one regulatory element of the construct while the CRISPR enzyme is linked to another regulatory module within the vector.

9. The method according to claim 1, wherein the engineered polynucleotide construct is administered using one or more of following delivery methods:

liposome encompassing the engineered polynucleotide construct, targeted liposome with a ligand specific to the plant pathogen on the external surface and encompassing the engineered polynucleotide construct to be administered, using nanoparticles comprising Silver and Gold, gene guns or micro-projectiles where the construct is adsorbed or covalently linked to heavy metals which carry it to different bacterial cells, or bacterial conjugation methods and bacteriophage specific to the targeted pathogen.

10. The method according to claim 1, wherein the first enzyme is a nicking enzyme and the second enzyme is a cleaving enzyme.

11. The method according to claim 1 further comprising the step identifying the set of nucleotide repeat sequences comprises:

selecting a nucleotide sequence stretches of a predefined length Rn from the genomes of strains of candidate pathogen with a difference in the start position of consecutive stretches Rni+1 and Rni as 5 nucleotides, wherein the predefined length refers to the length of a stretch of nucleotide sequence picked from the complete nucleotide sequence of a bacterial genome, used as a seed input for local sequence alignment tools, aligning a stretch of sequences with the bacterial genome using a local alignment tool to find the location of the set of nucleotide repeat sequences in genomes of *Pseudomonas syringae* or *Xanthomonas axonopodis*, and identifying the set of nucleotide repeat sequences, repeating more than 10 times at distant locations on the bacterial genome as the set of nucleotide repeat sequences, wherein the set of nucleotide repeat sequences with repeats comprising of one or more of a Sequence ID 001, a Sequence ID 002, reverse complement of the Sequence ID 001, or a reverse complement of the Sequence ID 002.

12. The method according to claim 1, wherein the identified nucleotide repeat sequences are in genomic neighborhood of or flanking the genes encoding proteins with essential functions within a pathogen genome, wherein the genomic neighborhood refers to regions lying within a predefined number of genes to the selected nucleotide repeat sequence or the reverse compliment of the selected nucleotide repeat sequence on the candidate pathogen genome or lying within a distance of predefined number of bases with respect to the selected nucleotide repeat sequence on the genome of the pathogen wherein, the important functional genes refer to the genes in pathogens which encode for proteins which are critical for survival, pathogenicity, interaction with the host, adherence to the host or for the virulence of bacteria, wherein the minimum predefined number of genes to be considered in genomic neighborhood is 10.

13. The method according to claim 1, wherein the set of nucleotide repeat sequences corresponding to one or more than one strain of the plant pathogen or candidate genus or species, wherein the set of nucleotide repeat sequences are found in multiple copies at distant locations on the genomes of all pathogenic strains of candidate genus or specie and these nucleotide repeat sequences do not show more than two nucleotide sequence similarity based matches to genome sequences corresponding to genera or species other than the genome of the candidate genus or species or with genomes of commensal strains within the candidate genus or species.

14. The method according to claim 1, wherein the distant locations may refer to distance of greater than 10000 nucleotide base pairs.

15. The method according to claim 1, wherein the non-culturable taxonomic groups or pathogens within a sample collected from an environment can be obtained by amplification of marker genes like 16S rRNA within bacteria.

16. The method according to claim 1, wherein the information and detection of non-culturable taxonomic groups or pathogens within a sample can be obtained by the binning of whole genome sequencing reads into various taxonomic groups using different methods including sequence similarities as well as several methods using supervised and unsupervised classifiers for taxonomic binning of metagenomics sequences.

17. A system for combating infections due to a plant pathogen, the system comprises:

a sample collection module for obtaining a sample from an infected area;

a pathogen detection and DNA extraction module isolating DNA from the obtained sample using one of a laboratory methods;

a sequencer for sequencing the isolated DNA;

one or more hardware processors;

a memory in communication with the one or more hardware processors, wherein the one or more first hardware processors are configured to execute programmed instructions stored in the one or more first memories, to:

identify a set of nucleotide repeat sequences in the sequenced DNA which occur more than a predefined number of times in the plant pathogen;

identify a set of neighborhood genes present upstream and downstream of the set of nucleotide repeat sequences;

annotate the set of neighborhood genes according to their functional roles in their respective pathogen based on their involvement in pathways in the identified set of neighborhood genes; and test presence of a secondary structure in the identified set of nucleotide repeat sequences;

an administration module for preparing and administering an engineered polynucleotide construct on the infected plant to combat the infections due to the plant pathogen, wherein the engineered polynucleotide construct is comprising:

one or more of the set of nucleotide repeat sequences with multiple copies dispersed in nucleotide sequences of genomes of *Pseudomonas syringae* or *Xanthomonas axonopodis*, wherein the set of nucleotide repeat sequences comprises one or more of a Sequence ID 001, reverse complement of the Sequence ID 001, Sequence ID 002, reverse complement of the Sequence ID 002, a first enzyme capable of nicking and cleaving the identified set of nucleotide repeat sequences, and a second enzyme capable of removal of a set of neighborhood genes flanking the set of nucleotide repeat sequences; and an efficacy module for check the efficacy of the administered engineered polynucleotide construct to combat the plant pathogen after a predefined time period, and re-administer the engineered polynucleotide construct if the plant pathogen is still present in the infected plant post administering.

* * * * *